(12) United States Patent
Jin et al.

(10) Patent No.: US 10,350,427 B2
(45) Date of Patent: Jul. 16, 2019

(54) RTMS DEVICE

(71) Applicant: Newport Brain Research Laboratory Inc., Newport Beach, CA (US)

(72) Inventors: Yi Jin, Irvine, CA (US); Charles Knezevich, Spring Valley, CA (US); Robert D. Silvetz, San Diego, CA (US); Mark Chien, Cerritos, CA (US)

(73) Assignee: Kosivana Holdings Limited, Limassol (CY)

( * ) Notice: Subject to any disclaimer, the term of this patent is extended or adjusted under 35 U.S.C. 154(b) by 772 days.

(21) Appl. No.: 13/858,783

(22) Filed: Apr. 8, 2013

(65) Prior Publication Data

US 2013/0289433 A1 Oct. 31, 2013

Related U.S. Application Data

(60) Provisional application No. 61/621,413, filed on Apr. 6, 2012.

(51) Int. Cl.
*A61N 2/00* (2006.01)
*A61N 2/02* (2006.01)
*A61B 5/0478* (2006.01)

(52) U.S. Cl.
CPC ............ *A61N 2/004* (2013.01); *A61B 5/0478* (2013.01); *A61N 2/008* (2013.01); *A61N 2/02* (2013.01)

(58) Field of Classification Search
CPC .......... A61N 2/006; A61N 2/02; A61N 2/004; A61N 2/008; A61N 1/36025; A61N 1/36096; A61N 1/36082; A61N 1/0476; A61N 1/0484; A61N 1/0534; A61B 5/0478; A61B 5/6803
See application file for complete search history.

(56) References Cited

U.S. PATENT DOCUMENTS 8,465,408 B2 6/2013 Phillips et al.
8,475,354 B2 7/2013 Phillips et al.
8,480,554 B2 7/2013 Phillips et al.
(Continued)

FOREIGN PATENT DOCUMENTS

JP 2008543416 A 12/2008
WO 2006134598 A2 12/2006
(Continued)

OTHER PUBLICATIONS

Phys.org "Physicists show electrons can travel over 100 times faster in graphene than in silicon" dated Mar. 24, 2008, accessed online at http://phys.org/news/2008-03-physicists-electrons-faster-graphene-silicon.html on Jul. 18, 2018.*
Chi, Yu Mike et al., "Dry-contact and noncontact biopotential electrodes: methodological review," *IEEE Reviews in Biomedical Engineering*, 2010, 3:106-119.
(Continued)

*Primary Examiner* — Kaylee R Wilson
(74) *Attorney, Agent, or Firm* — Saliwanchik, Lloyd & Eisenschenk (57) ABSTRACT

An rTMS coil or set of coils are designed to affect multiple regions of the brain with synchronous magnetic field pulses. Multiple coils aligned over the targeted regions of interest, or a single coil that is stretched or enlarged in a shape that allows the magnetic field to affect the areas of interest are disclosed. Also disclosed is a method of optimizing repetitive transcranial magnetic stimulation (rTMS) treatments.

6 Claims, 8 Drawing Sheets

(56) References Cited

U.S. PATENT DOCUMENTS

| | | | |
|---|---|---|---|
| 8,585,568 B2 | 11/2013 | Phillips et al. | |
| 8,690,748 B1 * | 4/2014 | Fu | A61N 1/0476 600/15 |
| 8,870,737 B2 | 10/2014 | Phillips et al. | |
| 8,888,672 B2 | 11/2014 | Phillips et al. | |
| 8,888,673 B2 | 11/2014 | Phillips et al. | |
| 8,926,490 B2 | 1/2015 | Phillips et al. | |
| 8,961,386 B2 | 2/2015 | Phillips et al. | |
| 2007/0225776 A1 | 9/2007 | Fritsch et al. | |
| 2008/0200749 A1 | 8/2008 | Zheng et al. | |
| 2009/0112281 A1 | 4/2009 | Miyazawa et al. | |
| 2010/0185042 A1 | 7/2010 | Schneider et al. | |
| 2010/0185256 A1 | 7/2010 | Hulvershorn | |
| 2010/0210894 A1 | 8/2010 | Pascual-Leone et al. | |
| 2010/0256438 A1 | 10/2010 | Mishelevich et al. | |
| 2010/0286470 A1 | 11/2010 | Schneider et al. | |
| 2011/0082326 A1 | 4/2011 | Mishelevich et al. | |
| 2011/0319700 A1 | 12/2011 | Schneider | |
| 2012/0053449 A1 | 3/2012 | Moses et al. | |

FOREIGN PATENT DOCUMENTS

| | | | | |
|---|---|---|---|---|
| WO | WO 2006134598 A2 * | 12/2006 | | A61N 2/006 |
| WO | WO 2009/023680 A1 | 2/2009 | | |
| WO | WO-2009/023680 A1 | 2/2009 | | |
| WO | WO 2012/048319 A2 | 4/2012 | | |
| WO | WO 2013/006670 A2 | 1/2013 | | |
| WO | WO 2013/038400 A1 | 3/2013 | | |
| WO | WO 2013/121359 A2 | 8/2013 | | |

OTHER PUBLICATIONS

Sullivan, Thomas J. et al., "A brain-machine interface using dry-contact, low noise EEG sensors," *IEEE International Symposium on Circuits and Systems*, Jun. 2008, p. 1986-1989.

Tada, K. et al., "Graphene magnet realized by hydrogenated graphene nanopore arrays," *Applied Physics Letters*, 2011, 99(18):1-3.

Belle, D., "Graphene goes magnetic." nanotechweb.org.Nov. 17, 2011. <URL = http://nanotechweb.org/cws/article/tech/47854>.

* cited by examiner

RTMS DEVICE

CROSS-REFERENCE TO RELATED APPLICATIONS

The present application claims priority under 35 U.S.C. § 119(e) to U.S. Provisional Applications No. 61/621,413, filed on Apr. 6, 2012 the disclosure of which is incorporated herein by reference in its entirety.

FIELD OF THE INVENTION

The present invention relates to novel repetitive transcranial magnetic stimulation (rTMS) devices that are capable of stimulating two or more regions in the brain of a patient treated with such a device. The present invention also relates to graphene phased array magnets.

BACKGROUND OF THE INVENTION

Transcranial magnetic stimulation (TMS) is a procedure that uses magnetic fields to stimulate nerve cells in the brain to improve symptoms of depression and other neuropsychiatric conditions. Traditionally, TMS coils have been of a circular or figure-8 shape, designed to achieve maximum strength at a single point. For treatment of depression with standard TMS, a large electromagnetic coil is placed against or near the scalp near the forehead. The electromagnet used in TMS creates electric currents and magnetic fields that stimulate nerve cells in the region of your brain involved in mood control and depression.

The design of TMS coils can vary based on, for example, the type of material used to construct the core of the coil, the geometry of the coil configuration and the characteristics of the pulse produced by the coil. The coil is generally composed of a ferromagnetically active material and is generally called a 'solid-core' design. Several different types of coils exist, each of which produce different magnetic field patterns which include round coils, figure-eight coils, double-cone coils and four-leaf coils. Design variations in the shape of the TMS coils allows for variable penetration of the brain with the magnetic field generated by the coils. TMS devices generally are configured to treat one area of the brain at a time. In cases where multiple areas of the brain are desired to be treated then sequential treatments of the different regions of the brain are required.

The present invention provides novel rTMS devices that are capable of stimulating two or more regions in the brain of a patient treated with such a device when rTMS is required to generate synchronous TMS pulses that affect multiple regions of the brain.

SUMMARY OF THE INVENTION

Briefly, in accordance with the present invention, a repetitive transcranial magnet stimulation (rTMS) device is used to treat neuropsychiatric conditions or to improve physiological functions wherein the device contains a housing that conforms to the shape of a head of a patient or a portion of the patient's head and a coil to deliver a magnetic field. The coil configuration produces a magnetic field capable of delivering magnetic stimulation to two or more regions of a brain of a patient fitted with the rTMS device. The coil configuration comprises 2 or more coils or alternatively a single coil that is shaped to deliver magnetic stimulation to two or more regions of the brain of the patient. The geometry of the coil configuration can be a phased-array of magnetic field emitting devices, allowing complex geometries and emission fields.

Additionally, the rTMS device of the present invention can be a cap worn by a patient that has a plurality of graphene magnetic emitters that make up an array. The cap is made of any fabric such as a cloth fabric mesh. Synthetic polymer meshes can also be used. The emitters are affixed to the cap to make an array of emitters across the whole head of the patient. The cap is worn on the head of the patient where the emitters can produce desired magnetic fields by programming software that controls each emitter. The array's elements are driven by software that turns on and off each emitter to optimize the shape and placement of the magnetic lobes resulting in a phased array. The cap can additionally be fitted with touch-less EEG sensors so that a patient's EEG can be monitored in addition to providing rTMS.

The rTMS device of the present invention can deliver magnetic stimulation to the front and rear regions of the brain; the motor cortex and frontal cortex regions of the brain; or the lateral sides of the frontal lobe region of the brain. Preferably, the coil configuration is synchronized to promote coherence and synchronous behavior between multiple locations in the brain.

The present rTMS device can be used to enhance or improve physiological functions and to treat neuropsychiatric disorders or conditions. Physiological functions include concentration, sleep, alertness, memory, blood pressure, stress, libido, speech, motor function, physical performance, cognitive function, intelligence, height (in children) and weight. A neuropsychiatric condition or disorder includes Autism Spectrum Disorder (ASD), Alzheimer's disease, ADHD, schizophrenia, anxiety, chronic pain, depression, coma, Parkinson's disease, substance abuse, bipolar disorder, a sleep disorder, an eating disorder, tinnitus, traumatic brain injury, post traumatic stress syndrome, and fibromyalgia.

Of particular interest in practicing the present invention is an rTMS device that is used to treat disorders that have poor coherence across different regions of the brain, such as, for example, Alzheimer's disease, speech and language disorders, schizophrenia and depression, by providing a device that can treat 2 or more regions of the brain simultaneously.

DETAILED DESCRIPTION OF THE INVENTION

In practicing the present invention, a repetitive transcranial magnetic stimulation (rTMS) device is made to contain a housing that conforms to the shape of a head of a patient and/or to one or more portions of a human head. Different sizes can be made to treat pediatric, adolescent and adults. The present device also contains a coil to deliver a magnetic field. The coil configuration produces a magnetic field capable of delivering magnetic stimulation to two or more regions of a brain of a patient fitted with the rTMS device. The coil configuration can be 2 or more coils or, alternatively, a single coil that is shaped to deliver magnetic stimulation to two or more regions of the brain of the patient. Alternatively, the geometry of the coil configuration may be a phased-array of magnetic field emitting devices, allowing complex geometries and emission fields. Graphene-based magnets are also useful in the practice of the present invention.

Figure 5:
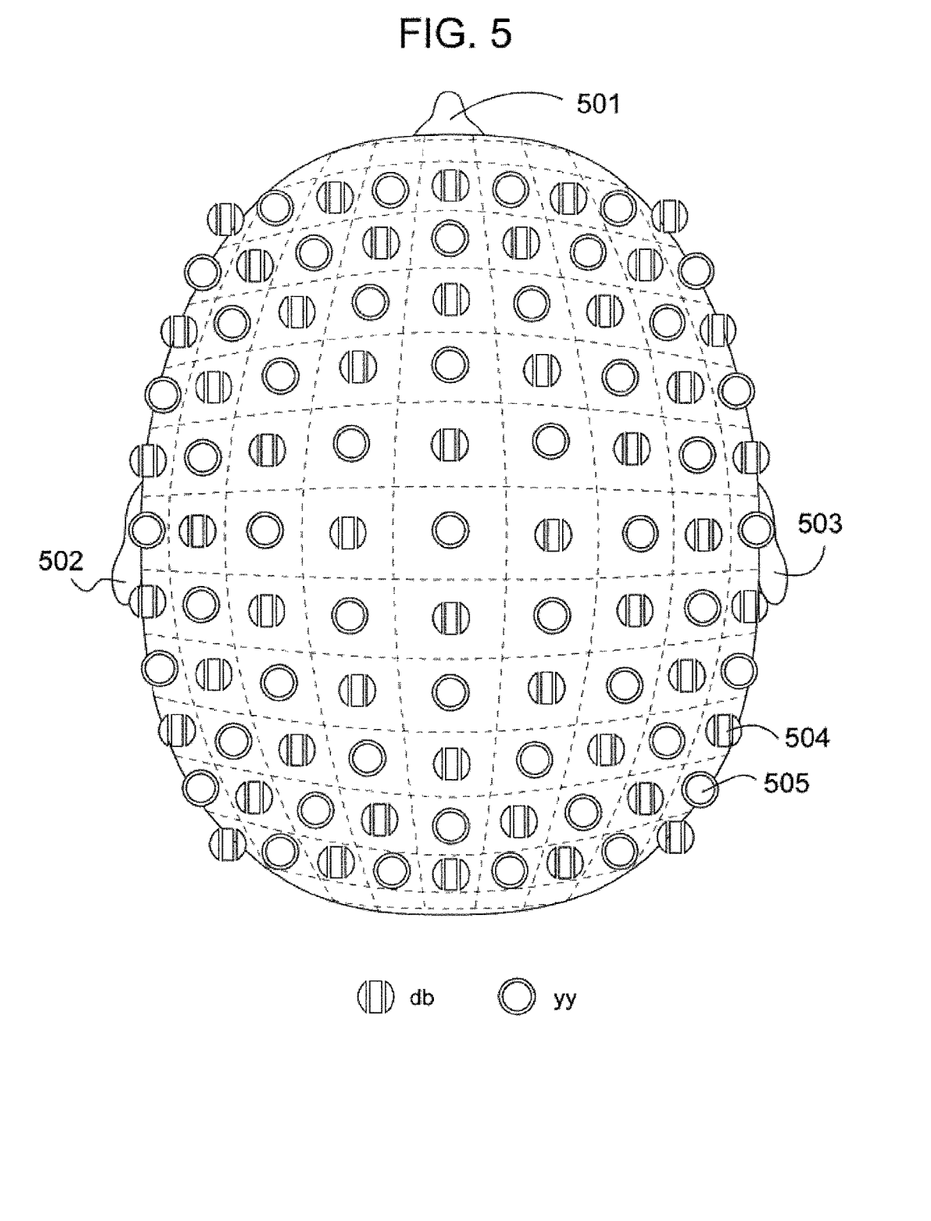
FIG. 5 is a top view of a patient wearing a rTMS cap that contains two types of graphene emitters.

In a preferred embodiment of the present invention, the rTMS device is a hat or a cap worn by a patient where the cap has a plurality of magnetic graphene emitters that make up an array. The cap is made of any fabric such as a cloth fabric mesh. Synthetic polymer meshes can also be used. The emitters are affixed to the cap to make an array of emitters across the whole head of the patient. The cap is worn on the head of the patient where the emitters can produce desired magnetic fields by programming software that controls each emitter. The array's elements are driven by software that turns on and off each emitter to optimize the shape and placement of the magnetic lobes resulting in a phased array. FIG. 5 shows a top view of an rTMS cap fitted on a patient where the nose 501 is seen at the top of the drawing and the ears 502, 503 are seen at the sides.

The present emitters are used to create a flat-foot-print, curved placement, coordinated phased-array using graphene emitters. Graphene (carbon nano-tube fibers) wire is used to make small coils. Because of the very low resistance that graphene has and the nano structure of the graphene fibers, very small electromagnetic coils can be made as opposed to current electromagnetic coils which require large diameter wires in order to reduce the resistance that result in bulking, heavy coils. The small size of the graphene electromagnetic coils allows for many unique applications especially when combined with sensors. Such applications include but are not limited to medical applications employing magnetic stimulation, industrial processing, biological mixing, breaking up biofilms, colloidal processing, magneto drives and the like. In such applications the graphene electromagnetic coils can be made in different spatial configurations where each configuration creates a specific magnetic field. The use of differently shaped graphene electromagnetic coils can be used to optimize overall magnetic field direction properties desired for any given application.

Figure 1:
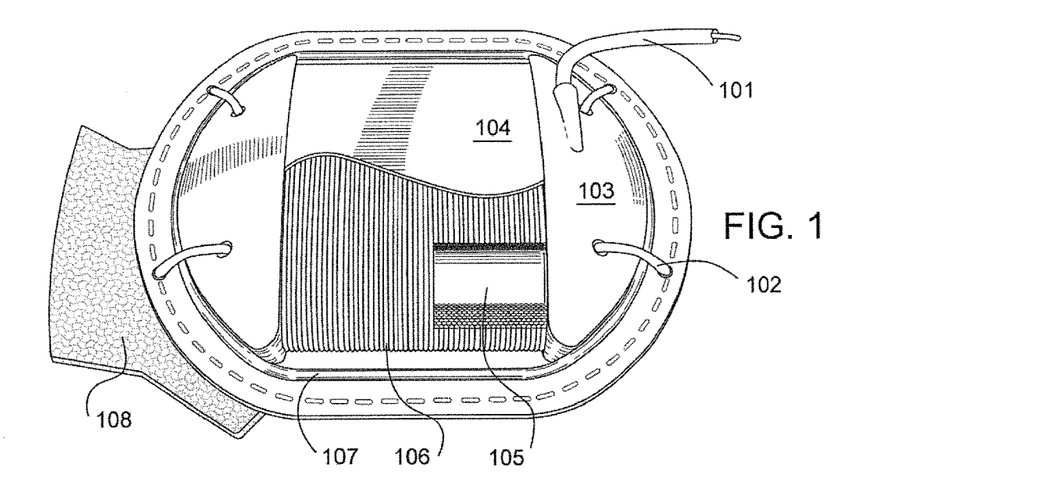
FIG. 1 shows an embodiment of a db graphene emitter.

One type of graphene electromagnetic coil or graphene emitter is shown in FIG. 1 which is called a dog-bone (db) emitter where the graphene fibers are coiled in a dog-bone shape. In FIG. 1 an oblong central shaft 105 is covered with graphene fiber coils (emitters) 106 and is contained in winding disc 103. A magnetic radiating shell 104 covers the graphene coils 106. A cable strain relief 101 runs to a processing unit (not shown). Rim 107 contains the winding disc and is attached to a substrate 108 by threads 102. The substrate is any materials where it is desired to have the db emitter in use such as, for example, a cap in the application of an rTMS device as described herein. When electricity is passed through the db emitter the magnetic field spills out of the ends of the emitter and the lobes are wide and globular. In a TMS application this would produce skull penetration and will attract or repel other lobes from other emitters back to the brain.

Figure 2:
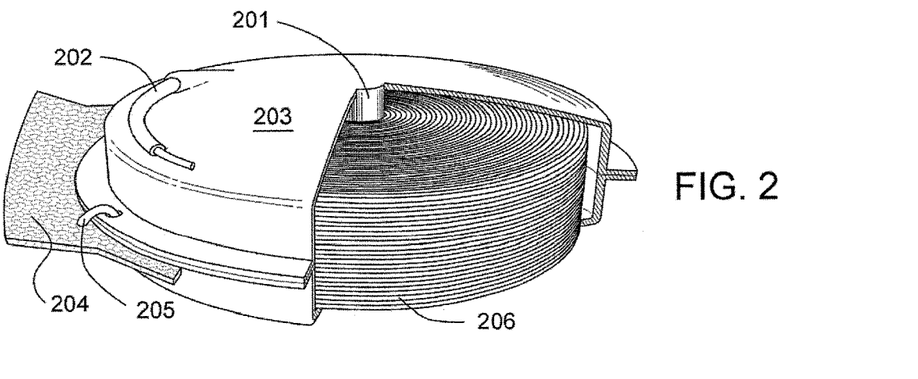
FIG. 2 shows an embodiment of a yy graphene emitter.

Another type of graphene electromagnetic coil or graphene emitter is shown in FIG. 2 which is called a yo-yo (yy) emitter where the graphene fibers are coiled in a shape like a yo-yo string would be attached to a yo-yo. In FIG. 2 a round central shaft 201 is covered with graphene fiber coils (emitters) 206 and is contained in a magnetic radiating shell 203. A cable strain relief 202 runs to a processing unit (not shown). The emitter is attached to a substrate 204 by thread 205. The substrate is any material where it is desired to have the db emitter in use such as for example a cap in the application of a TMS device as described herein. When electricity is passed through the yy emitter, the majority of the magnetic field spills out of the ends of the round shaft 201 perpendicular to the graphene fiber coils 206. In an rTMS application one half of the generated magnetic field would be directed to the skull and the other half away from the head.

Figure 3:
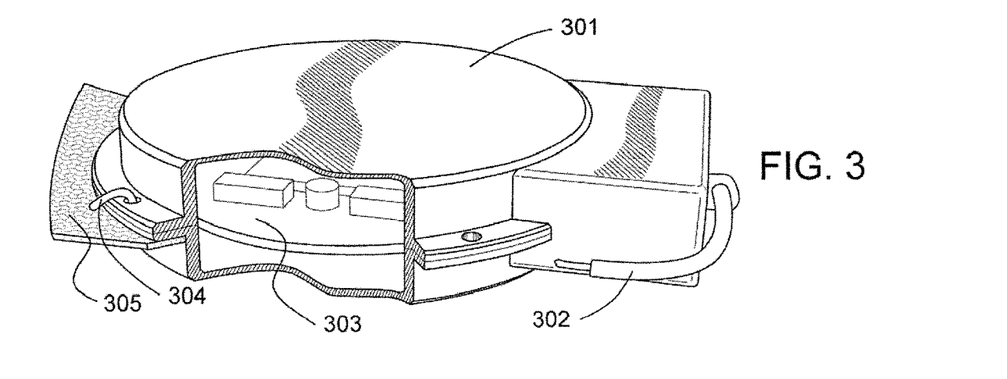
FIG. 3 shows a touch-less EEG sensor.

The present graphene electromagnetic coils are preferably used with a sensor where the particular sensor would be chosen for the particular use of the coils. For TMS application a touch-less dry electrode EEG sensor would be used in combination with the graphene emitters. Touch-less dry electrode EEG sensors are commercially available from Cognionics, San Diego, Calif. FIG. 3 shows an EEG touch-less dry-electrode EEG sensor that contains a PCB board 303 housed in an EEG sensor shell 301. A cable strain relief 302 runs to a processing unit (not shown). The sensor is attached to a substrate 305 by thread 304.

In a preferred embodiment of the present invention, db emitters, yy emitters and touch-less dry electrode EEG sensors are used to make a TMS cap that can both detect EEG patterns and administer transcranial magnetic stimulation to a patient by producing a phased array effect.

Figure 4:
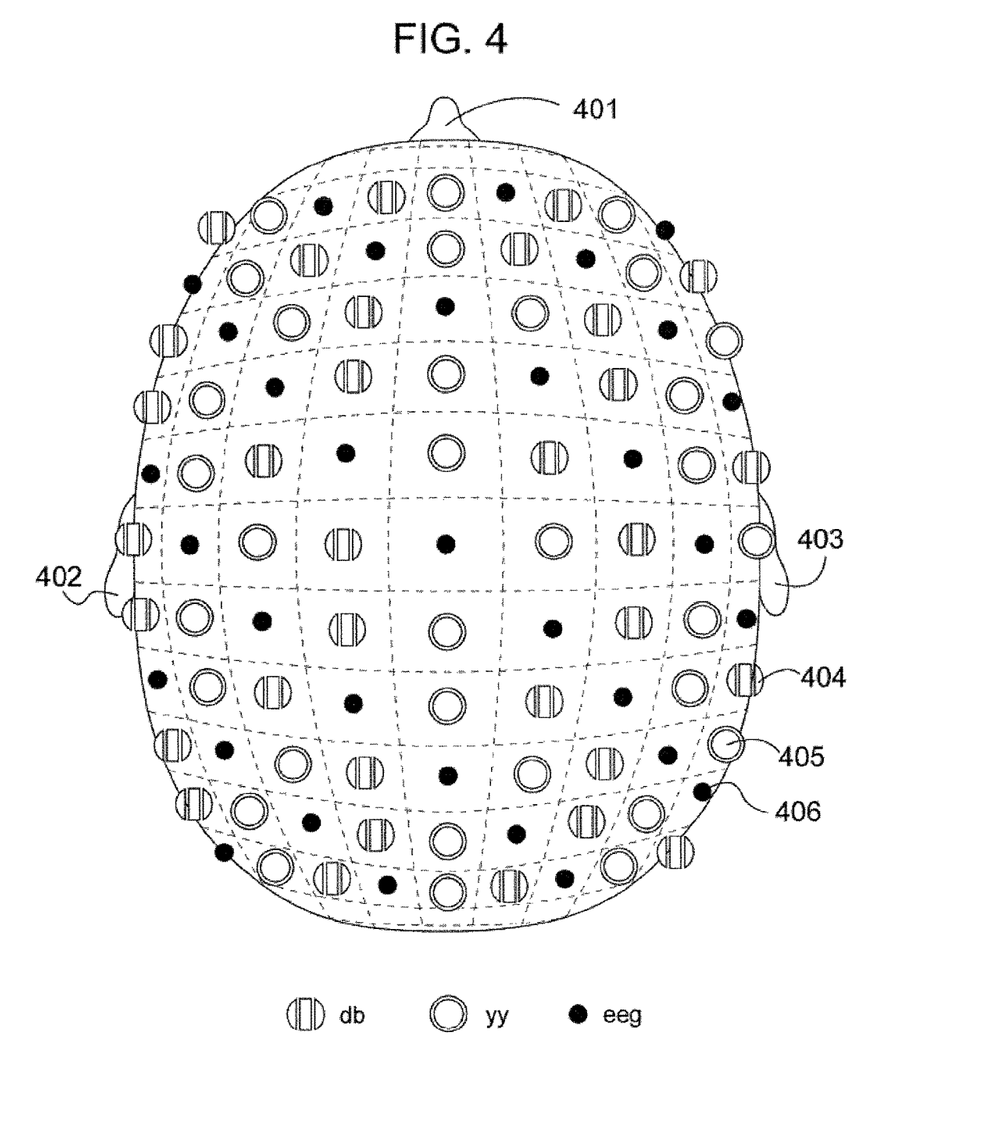
FIG. 4 is a top view of a patient wearing a rTMS cap that contains two types of graphene emitters and touch-less EEG sensors.

As shown in FIG. 4, each emitter 404, 405 and EEG sensor 406 is a generally flat disc 404, 405 and 406 that is in the basic shape of a circle. The emitters and sensors are butted-up against each other, attached to the fabric mesh, and vary in starting sequence and vary in position from row to row. The emitters 404, 405 and sensors 406 are connected by wires (not shown) to a control panel (not shown) that contains the programmed software and power supply. There are two types of emitters shown in FIG. 4 and are named herein based on their shape. One is referred to as the dog-bone (db) emitter 404 and the other is referred to as the yo-yo (yy) emitter (405). There are two preferred patterns for placing the emitters and sensors on the cap: (1) -[db]-[eeg]-[yy]- and (2) -[yy]-[eeg]-[db]-. The basic pattern that is laid-down and attached is follows:

-[db]-[eeg]-[yy]-[db]-[eeg]-[yy]-[db]-[eeg]-[yy]-
-[db]-[yy]-[eeg]-[db]-[yy]-[eeg]-[db]-[yy]-[eeg]-
-[eeg]-[yy]-[db]-[eeg]-[yy]-[db]-[eeg]-[yy]-[db]-
-[db]-[eeg]-[yy]-[db]-[eeg]-[yy]-[db]-[eeg]-[yy]-
-[db]-[yy]-[eeg]-[db]-[yy]-[eeg]-[db]-[yy]-[eeg]-
-[eeg]-[yy]-[db]-[eeg]-[yy]-[db]-[eeg]-[yy][db]-

The emitters 404, 405 and sensors 406 are sewn on, or attached by other means, like buttons, over the whole cloth mesh fitted to cover a head. The sensors and emitters should not overlap. An average size cap will contain 45 eeg sensors, 45 Db emitters, and 45 Yy emitters.

The two types of emitters, db and yy, produce an array that is used to shape and optimize the magnetic field direction. This "Phased-Array" is controlled by software and the magnetic field can be adjusted accordingly. The phasing of the magnetic array is accomplished through software control of the magnitude, position and orientation of each separate emitter, in sequence, through time. Since opposite fields attract each other, the lobes can effectively be focused to a targeted area of the scalp and underlying brain structures. The size of the emitters and sensors is not critical to the practice of the present invention. The diameter of the emitters and sensors is typically in the range of 15-30 millimeters (mm) and preferably 17-19 mm. An average size cap will contain about 45 eeg sensors, 45 db emitter and yy emitters.

In the yy emitters the majority of the magnetic field spills out the ends of the post, perpendicular to the direction of the disks. So half of the field tends toward the direction of the brain, as the yy emitter lays on its side, against the head and the other half out into space away from the brain. In the db emitters the opposite happens. The magnetic field spills out the ends of the db emitter tending toward parallel to the side of the skull where the lobes still are fairly wide, and globular providing skull penetration. More importantly the db emitters are better in attracting, or repelling, other lobes back towards the brain, and determining the direction of lobes in the phased-array.

The focusing of these arrays of magnetic lobes is useful in the practice of the present invention. As an example a cluster of 3-7 of the yy emitters will drive the primary magnetic lobes on one side of the head. The db emitters on the same side will help shape and stretch these primary lobes. The yy and db emitters on the other side of the head will shape and stretch the lobes to the preferred target areas in greatest concentration, hence phased-arrays.

FIG. 5 shows is a top view of a patient wearing a TMS cap of the present invention that contains db emitters 504 and yy emitters 505 but no EEG sensors. Orientation of the cap is seen by the patient's nose 501 and ears 502, 503. The emitters 504, 505 are generally flat discs that are in the basic shape of a circle. The emitters are butted-up against one another, attached to the fabric mesh substrate, and vary in starting sequence and vary in position from row to row. The emitters 504, 505 are connected by wires (not shown) to a control panel (not shown) that contains the programmed software and power supply. Preferably, the emitters are arranged in an alternating configuration as depicted in FIG. 5. The emitters 504, 505 are sewn on, or attached by other means, like buttons, over the whole cloth mesh fitted to cover a head and should not overlap. An average size cap will contain about 125 or more emitters. This TMS cap is used to administer repetitive TMS to a targeted area of the brain.

Figure 6:
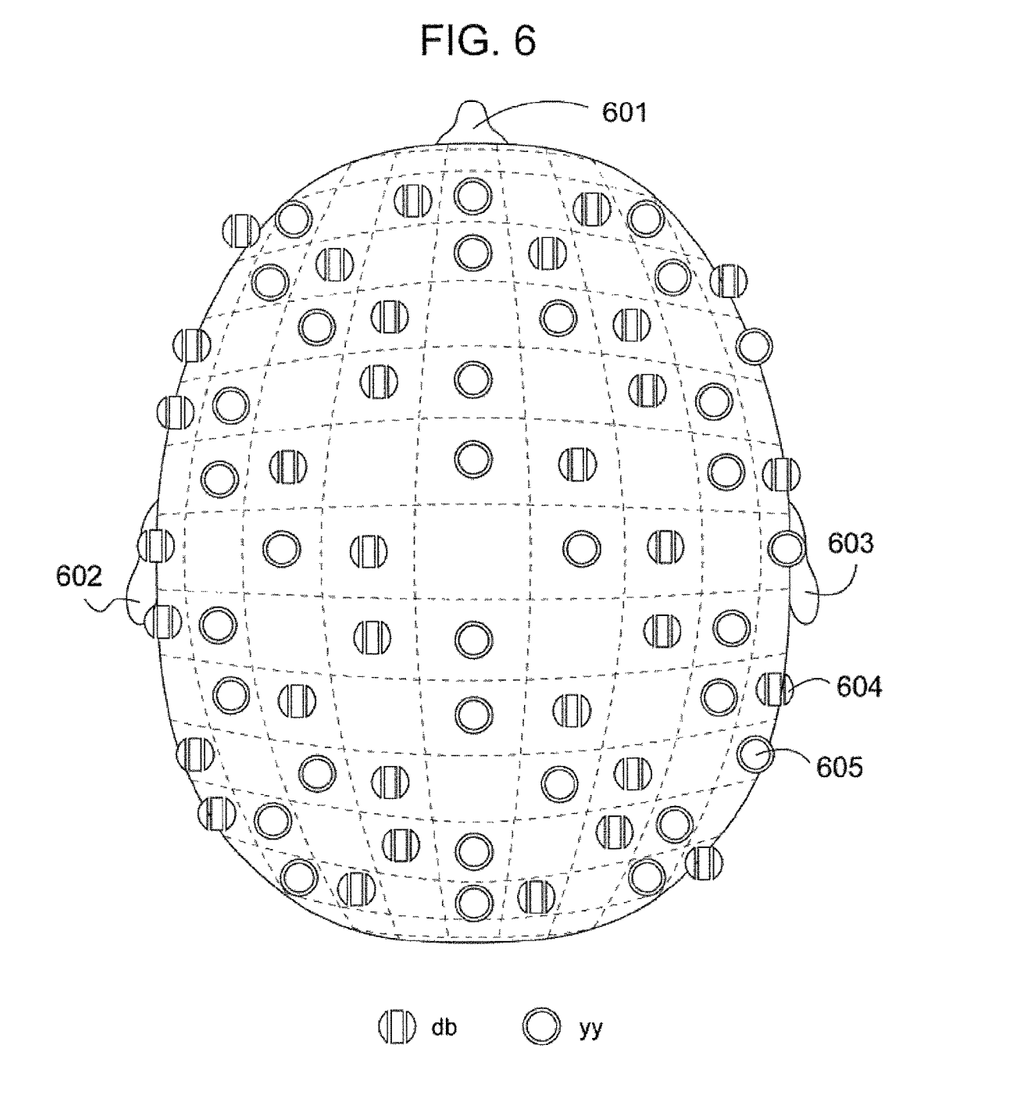
FIG. 6 is a top view of a patient wearing a rTMS cap that contains two types of graphene emitters.

FIG. 6 is another top view of a patient wearing a TMS cap of the present invention that contains db emitters 604 and yy emitters 605 but no EEG sensors. Orientation of the cap is seen by the patient's nose 601 and ears 602, 603. The emitters 604, 605 are generally flat discs that are in the basic shape of a circle. The emitters are butted-up against one another, attached to the fabric mesh substrate, and vary in starting sequence and vary in position from row to row. The emitters 504, 505 are connected by wires (not shown) to a control panel (not shown) that contains the programmed software and power supply. The embodiment shown in FIG. 6 is similar to the embodiment shown in FIG. 5 with the exception that less emitters are employed.

The focusing of these arrays of magnetic lobes is useful in the practice of the present invention. As an example a cluster of 3-7 of the yy emitters will drive the primary magnetic lobes on one side of the head. The db emitters on the same side will help shape and stretch these primary lobes. The yy and db emitters on the other side of the head will shape and stretch the lobes to the preferred target areas in greatest concentration, hence phased-arrays.

The rTMS device of the present invention can deliver, for example, magnetic stimulation to the front and rear regions of the brain; the motor cortex and frontal cortex regions of the brain; or the lateral sides of the frontal lobe region of the brain. Preferably, the coil configuration is synchronized to promote coherence and synchronous behavior, such as EEG wave patterns, between multiple locations in the brain.

The present rTMS device can be used to enhance or improve physiological functions and to treat neuropsychiatric disorders or conditions. Physiological functions include concentration, sleep, alertness, memory, blood pressure, stress, libido, speech, motor function, physical performance, cognitive function, intelligence, height (in children) and weight. A neuropsychiatric condition or disorder includes Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, post traumatic stress syndrome, and fibromyalgia.

Of particular interest in practicing the present invention is an rTMS device that is used to treat disorders that have poor coherence across different regions of the brain, such as, for example, Alzheimer's disease, speech and language disorders, schizophrenia and depression, by providing a device that can treat 2 or more regions of the brain simultaneously.

In one embodiment of the present invention an rTMS device is configured to treat an Alzheimer's patient by providing magnetic field stimulation to the front and rear portions of the brain. The patient is treated daily for 30 minutes with 6 seconds of magnetic stimulation per minute.

In another embodiment of the present invention an rTMS device is configured to treat a patient having a speech disorder by providing magnetic field stimulation to the motor cortex and the frontal cortex regions of the brain. The patient is treated daily for 30 minutes with 6 seconds of magnetic stimulation per minute.

In a further embodiment of the present invention an rTMS device is configured to treat a schizophrenic patient by providing magnetic field stimulation to the lateral sides of the frontal lobe of the brain. The patient is treated daily for 30 minutes with 6 seconds of magnetic stimulation per minute.

In another embodiment of the present invention an rTMS device is configured to treat a depressed patient by providing magnetic field stimulation to the lateral sides of the frontal lobe of the brain. The patient is treated daily for 30 minutes with 6 seconds of magnetic stimulation per minute.

There are several examples of disorders that result in EEG activity being incoherent or asynchronous between different brain regions. In Alzheimer's, activity between the front and rear portions of the brain tend to lack coherence. In speech and language disorders, the motor cortex is often asynchronous with the frontal cortex. In other disorders such as Schizophrenia or depression, there is often seen a lack of coherence between the lateral sides of the frontal lobe.

The symptoms of the disorder are reduced and improvement in cognitive function is achieved by administering the present rTMS pulses to entrain the regions to act in concert and synchronously.

The pulses generated by the present rTMS device to different regions of the brain are preferably synchronized together to promote coherence across the brain. The coils are oriented ergonomically with a tilt designed to fit the scalp. The rTMS device can contain multiple coils oriented to treat different regions of the brain or a single coil could be stretched so that the focus of the magnetic field is spread out in a line over a wider area. One example would be to stretch the coil so that it covers both lateral sides of the prefrontal lobe. If desired, the coil could be made larger which will cause the magnetic field to be more dispersed.

Figure 10A:
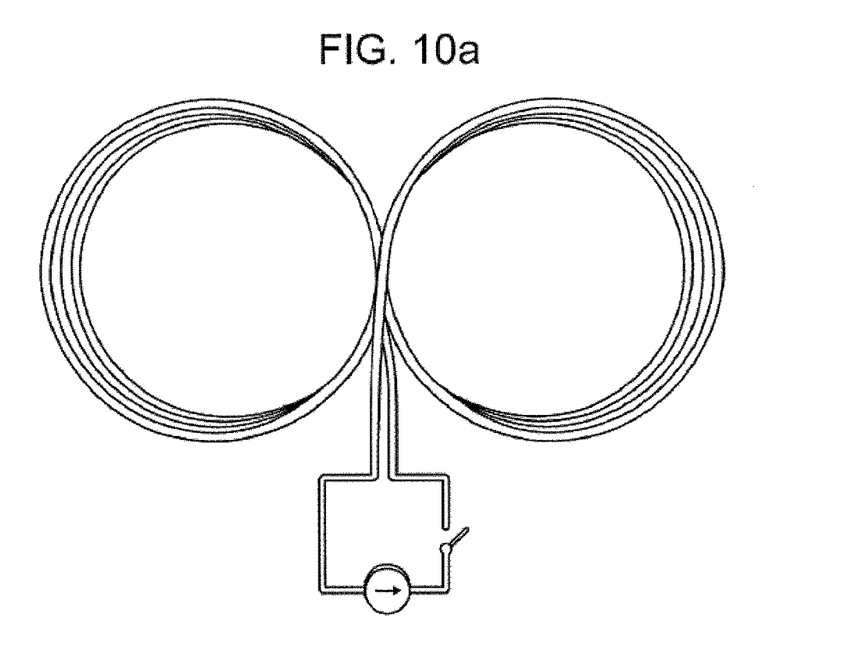
FIG. 10a shows a normal FIG. 8 coil and FIG. 10b shows an extended or elongated FIG. 8 coil that produces a magnetic field that stretches along the region underneath the coil, influencing all areas of the brain that lie within this region.
Figure 10B:
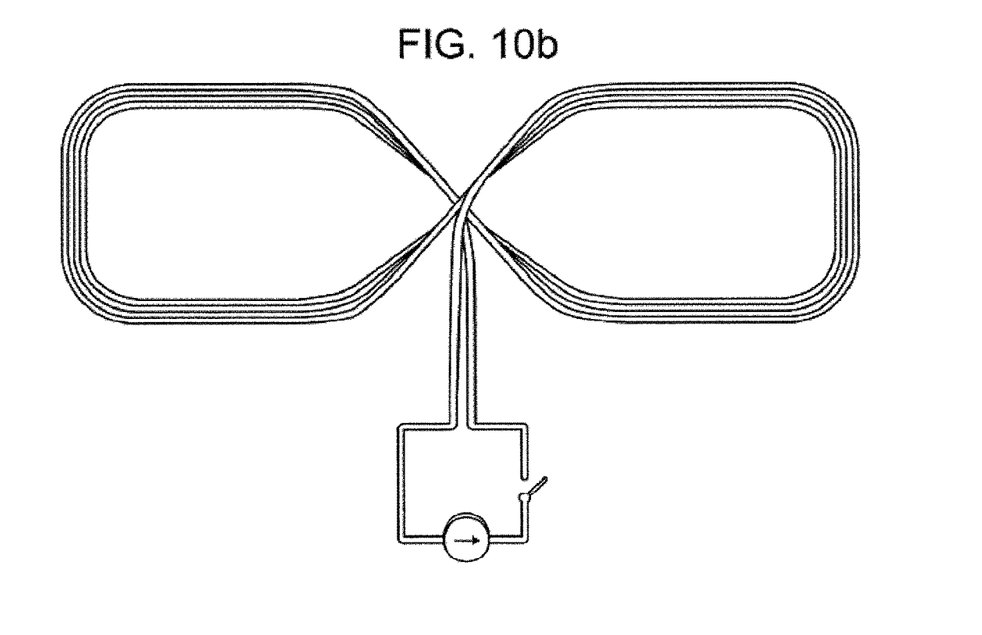

FIG. 10b shows an elongated coil that spreads the magnetic field underneath the coil to cover an area underneath the coil when used to administer rTMS to a patient. FIG. 10a is a traditional coil that does not cover the same area as the elongated coil. The coil shown in FIG. 10b can treat more than one area of the brain.

Figure 7:
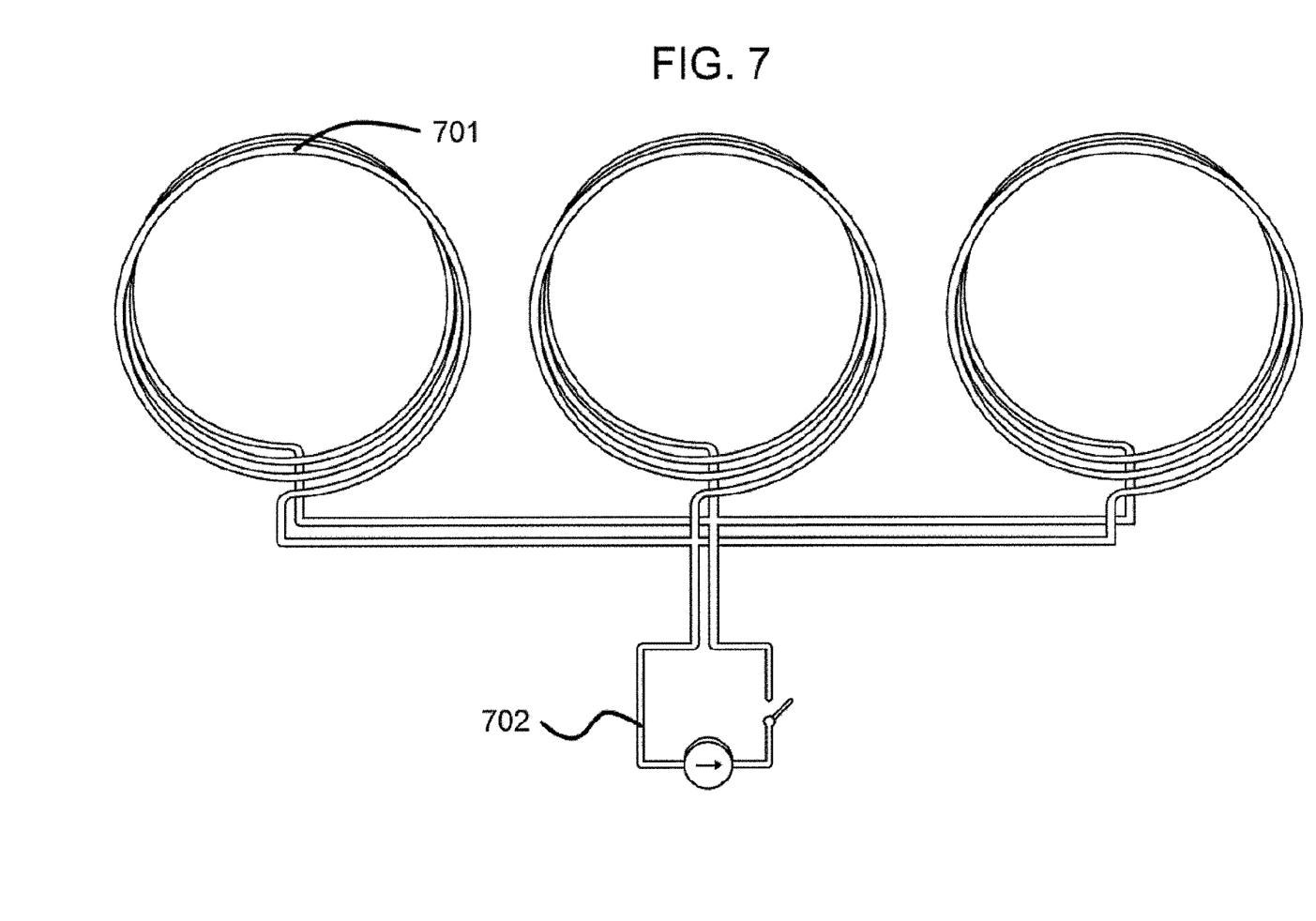
FIG. 7 shows a multi-loop coil that provides separate magnetic field sources at various regions of the brain. The coils are connected together so as to provide a set of synchronized magnetic fields across the brain.

FIG. 7 shows multiple coils connected together, situated to stimulate separate regions of the brain simultaneously.

Figure 8:
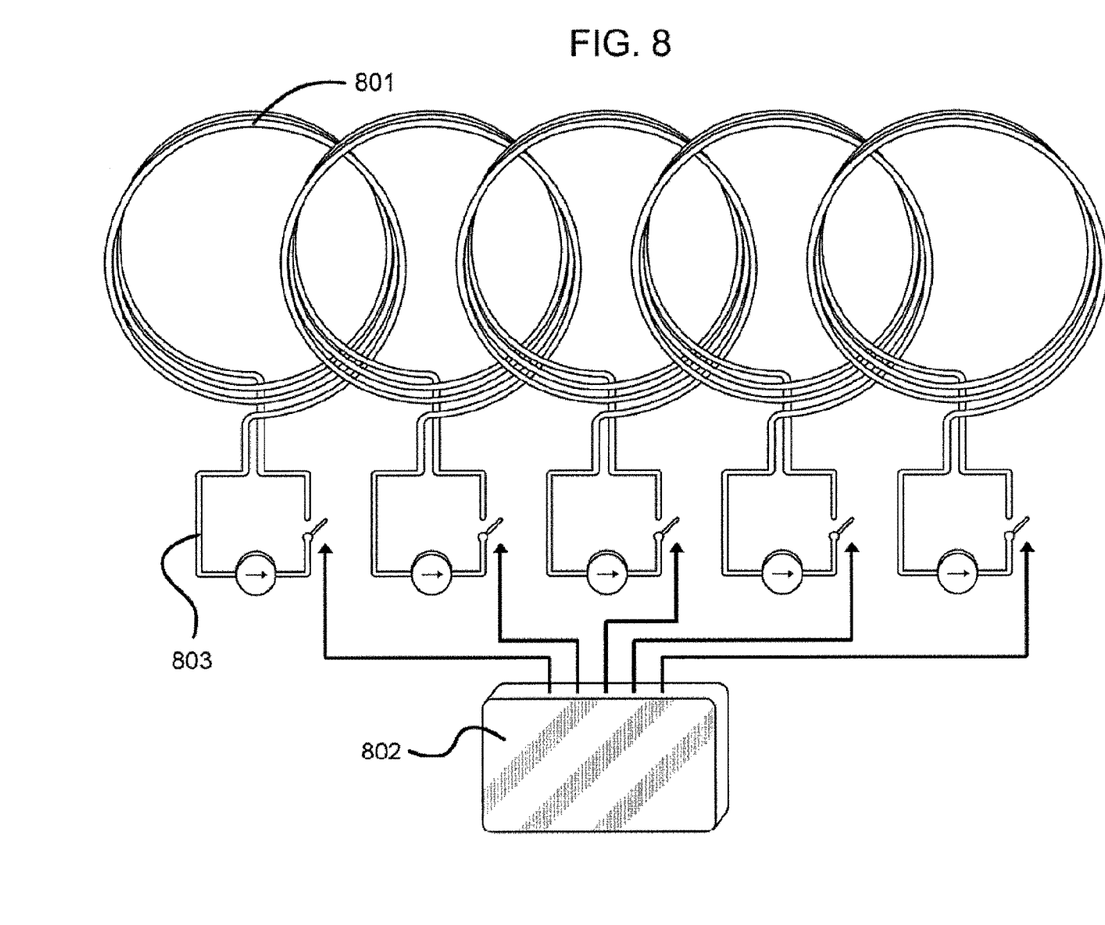
FIG. 8 shows a phased array configuration. In this configuration, the phase of the magnetic field pulses may be altered so as to provide additive or subtractive interference with each other, thereby creating a specific magnetic field pattern.

FIG. 8 shows a phased array of coils 801, intended to use phase differences in pulses to direct and target multiple regions of the brain. The coils are operated by a central processor 802 that can adjust the magnetic field produced by each coil. An on/off switch 803 is sued to turn off a particular coil if desired.

An additional aspect of the present invention is a method of optimizing repetitive transcranial magnetic stimulation (rTMS) of a patient by recording the patient's whole head EEG; mapping the energy of the EEG at one or more frequencies to identify regions of incoherent or non-synchronous brain activity; and administering rTMS to the regions of the brain that are incoherent and non-synchronous. Such an optimized process can include an rTMS device that has (a) 2 or more coils, (b) a single coil configured in such a way to deliver stimulation to distinct regions of the brain, or (c) a phased-array magnetic field emitting device capable of forming complex geometries and emission fields wherein the phased array modalities are leveraged to induce positional and temporal intensities. A preferred phased array is the rTMS cap described herein. With EEG mapping, areas of low energy are identified by measuring the energy of the EEG at the interested frequency across the brain employing well known algorithm selected from the group consisting of least squares, LORETA, and focal optimization. Areas of low energy can also be identified by measuring the Q-factor (width of the frequency plot) at the one or more frequencies used to map the energy of the EEG.

Figure 9:
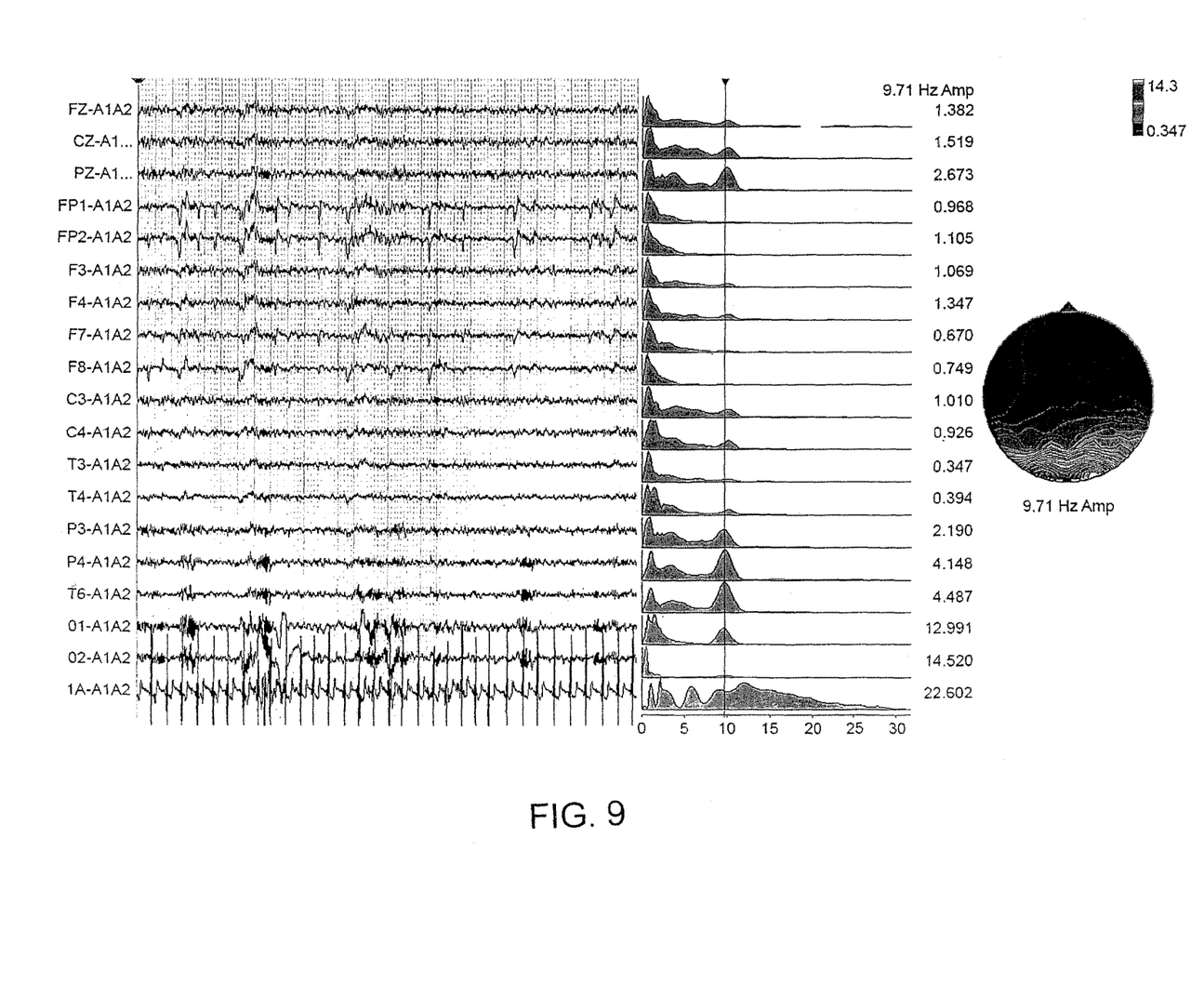
FIG. 9 shows the results of an EEG and brainwave map including the power distribution in a top view topography on an individual before treatment with rTMS.

FIG. 9 shows the results of an EEG and brainwave map including the power distribution in a top view topography on an individual before treatment with rTMS. The left panel shows the signals in time domain and the middle panel the frequency domain following Fast Fourier Transformation (FFT) where the dominant frequency is at 9.71 Hz. It can be seen that the dominant frequency of 9.71 is missing in some frontal channels. The right side map displays the power distribution in a top-view topography. The treatment is to convert the intrinsic frequency to a train of TTL pulses in a computer script file to trigger the TMS pulse discharge. The stimulation area will be the bilateral frontal lobe at a frequency of 9.71. The rTMS treatments started on a daily basis for 30 minutes will pull up the 9.71 Hz in those missing channels by providing stimulation at an harmonic of one of the biological signals.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A repetitive transcranial magnet stimulation (rTMS) device for treating a neuropsychiatric condition or to improve a physiological function, the rTMS device comprising:

a coil configuration that produces a magnetic field capable of delivering magnetic stimulation, at an rTMS pulse frequency, to two or more regions of a brain of a patient fitted with the rTMS device, wherein the rTMS device is configured to analyze recorded signals from the patient and determine, based on the recoded signals, a harmonic or subharmonic of a non-EEG biological metric of the patient, wherein the rTMS pulse frequency is the harmonic or subharmonic of the non-EEG biological metric, wherein pulses generated by the coil configuration are synchronized and promote coherence and synchronous behavior between multiple locations in the brain, wherein the coil configuration comprises 2 or more coils, and wherein each respective coil comprises an on/off switch.

2. The rTMS device of claim 1, wherein a geometry of the coil configuration is a phased-array of magnetic field emitting devices, allowing complex geometries and emission fields.

3. The rTMS device of claim 1, wherein the device is configured to deliver magnetic stimulation to the front and rear regions of the brain.

4. The rTMS device of claim 1, wherein the device is configured to deliver magnetic stimulation to the motor cortex and frontal cortex regions of the brain.

5. The rTMS device of claim 1, wherein the device is configured to deliver magnetic stimulation to the lateral sides of the frontal lobe region of the brain.

6. The rTMS device of claim 1, further comprising a recording device for recording the recorded signals from the patient.

* * * * *